United States Patent [19]

Cucchiaro et al.

[11] Patent Number: 5,518,008
[45] Date of Patent: May 21, 1996

[54] STRUCTURAL ANALYZER, IN PARTICULAR FOR MEDICAL IMPLANTS

[75] Inventors: Paul J. Cucchiaro, Beverly; Anthony DeLuzio, Milford, both of Mass.; Lawrence J. Dario, Barrington, R.I.; Stephen J. Cucchiaro, Beverly, Mass.

[73] Assignee: Spectral Sciences Research Corporation, Beverly, Mass.

[21] Appl. No.: 296,333

[22] Filed: Aug. 25, 1994

[51] Int. Cl.⁶ .................................................. A61B 5/103
[52] U.S. Cl. ............................... 128/777; 128/776
[58] Field of Search ................... 128/774, 776, 128/777, 781, 782, 739, 740, 744; 433/72, 215

[56] References Cited

U.S. PATENT DOCUMENTS

| | | | |
|---|---|---|---|
| 3,094,115 | 6/1963 | Polin . | |
| 4,470,810 | 9/1984 | Bourdeau et al. | 433/72 |
| 4,479,499 | 10/1984 | Alfano | 128/665 |
| 4,482,324 | 11/1984 | Wohlgemuth | 433/215 |
| 4,499,906 | 2/1985 | Wohlgemuth et al. | 128/777 |
| 4,637,256 | 1/1987 | Sugiyama et al. | 73/633 |
| 4,727,416 | 2/1988 | Cooper et al. | 358/98 |
| 4,764,114 | 8/1988 | Jeffcoat et al. | 128/776 |
| 4,837,732 | 6/1989 | Brandestini et al. | 364/413.28 |
| 4,840,563 | 6/1989 | Altendorf | 433/29 |
| 4,881,552 | 11/1989 | Heyman | 128/774 |
| 5,016,098 | 5/1991 | Cooper et al. | 358/98 |
| 5,049,070 | 9/1991 | Ademovic | 433/29 |
| 5,100,318 | 3/1992 | Demyun et al. | 433/72 |
| 5,106,302 | 4/1992 | Farzin-Nia et al. | 433/215 |
| 5,115,307 | 5/1992 | Cooper et al. | 358/98 |
| 5,230,621 | 7/1993 | Jacoby | 433/29 |

OTHER PUBLICATIONS

Schulte, W., et al., "Periotest to Monitor Osseointegration and to Check the Occlusion in Oral Implantology," *J. Oral Implantology*, 19(1):23–32 (1993).

Tse, F. S., et al., "Mechanical Vibrations Theory and Applications," pp. 51–55 (1978).

Product Information brochure from DATAQ Instruments, Inc., (Dec., 1993).

*Primary Examiner*—Max Hindenburg
*Attorney, Agent, or Firm*—Hamilton, Brook, Smith & Reynolds

[57] ABSTRACT

A dental analyzer for analyzing dental implants includes a dental probe having a probe tip for contacting a patient's dental implant. An accelerometer is coupled to the probe tip. A hammer fired by an actuator against the accelerometer impacts the probe tip against the dental implant which vibrates the dental implant. The accelerometer measures the acceleration time history of the vibrating dental implant. A processor converts the measured acceleration time history of the dental implant into a frequency spectrum from which a diagnosis can then be made regarding the condition of the dental implant.

35 Claims, 8 Drawing Sheets

STRUCTURAL ANALYZER, IN PARTICULAR FOR MEDICAL IMPLANTS

BACKGROUND

When a dental implant is implanted into the jaw bone of a patient, it is often difficult to determine whether sufficient bonding has occurred between the dental implant and the jaw bone. Currently, taking an x-ray of a patient's jaw and inspecting the x-ray for structural integrity between the dental implant and the jaw bone is a common method for determining whether a dental implant is properly bonded to the jaw bone. However, in cases where the progress of a dental implant must be followed over a period of time, the use of x-rays is undesirable due to medical considerations caused by the cumulative effect of multiple exposures to x-rays.

A number of attempts have been made to provide an apparatus for determining the mobility of a dental implant or tooth which does not require x-rays to be taken. One such attempt is found in U.S. Pat. No. 3,094,115, which discloses a tooth mobility indicator. In use, the patient sits in a dental chair with his head resting upon an oscillating element which vibrates the patient's teeth. A hand-held probe containing an accelerometer is placed upon a tooth to measure the amplitude of the vibrating tooth. The probe registers the departure of the amplitude and frequency of the signal received by the accelerometer from the input signal of the oscillating element. This method of measurement is subject to error due to variability in the placement of the oscillating element as well as distortion of the data measured through the patient's head and by the probe resonances themselves.

Another attempt is found in U.S. Pat. No. 4,470,810 which discloses a hand held probe for applying a motion to a tooth and measuring the displacement of the tooth from which the displacement rate of the tooth can be found. Since the displacement of a tooth is usually less than 1 millimeter, an instrument measuring such small displacements must be extremely accurate. However, displacement measurements measured with this probe use the probe itself as a reference point. As a result, the displacement measurements are subject to a high degree of error caused by variations in the angle at which the probe is held as well as the force at which the probe is pressed against the tooth.

A similar attempt is found in U.S. Pat. No. 4,881,552 which discloses a tooth stability monitor having a hand-held probe for assessing the rigidity of a tooth. The probe measures the displacement of the tooth and the resulting force applied to the tooth. This instrument is subject to the same errors experienced by the probe in U.S. Pat. No. 4,470,810.

Still another attempt is found in U.S. Pat. No. 4,482,324 which discloses a hand-held probe for determining the degree of looseness of a tooth. The instrument includes a ram which is disposed at a right angle with respect to the handle of the instrument. The ram is accelerated to a specific velocity and after impact against a tooth, the ram is repelled in a direction towards the initial position. The time required for the ram to return is a direct indicator of the degree of tooth mobility. This method is also subject to error due to variations in the manner which the probe is held relative to the tooth.

SUMMARY OF THE INVENTION

These attempts for determining the mobility of a tooth or dental implant through the use of a mechanical probe have not proven to be accurate or repeatable due to the parameter being measured, the method of measurement or the probe design. In order to accurately follow the progress of a dental implant over a period to time, the measuring instrument must be accurate enough to detect small changes in the condition of the dental implant. Accordingly, there is a continuing need for a mechanical instrument accurate enough to detect small changes in the condition of a dental implant such that the progress of a dental implant can be followed over a period of time.

The present invention provides a probe having a probe tip for contacting a structure. An accelerometer is coupled to the probe tip for measuring an acceleration time history of the structure. The probe includes an actuator for firing a hammer in order to impact the probe tip against the structure.

In preferred embodiments, a probe body comprising a hollow tube houses the actuator and the hammer. A membrane secured to the probe body supports the accelerometer and isolates motion of the accelerometer from motion of the probe body. The actuator includes an electromagnetic coil for positioning the hammer into firing position and a spring positioned against the hammer for firing the hammer. A sensor prevents the actuator from firing the hammer until the probe tip is pressed against the structure at a predetermined force. A processor converts the measured acceleration time history of the structure into a frequency spectrum through a Fourier transform function. Characteristics of the generated frequency spectrum are compared with a database of frequency spectrums enabling a diagnosis to be made.

The present invention probe is capable of analyzing a dental implant in a manner which is extremely accurate such that small changes in the condition of the dental implant can be detected. As a result, progress of a dental implant can be accurately followed over a period of time. The present invention, by measuring the acceleration time history of a dental implant, acquires enough data to provide information such as stiffness, mobility, damping, resonant modes/frequencies and osseointegration of a dental implant. Additionally, the present invention probe is capable of accurately analyzing the condition of any other medical implant, teeth, bones or mechanical structures used in industry.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
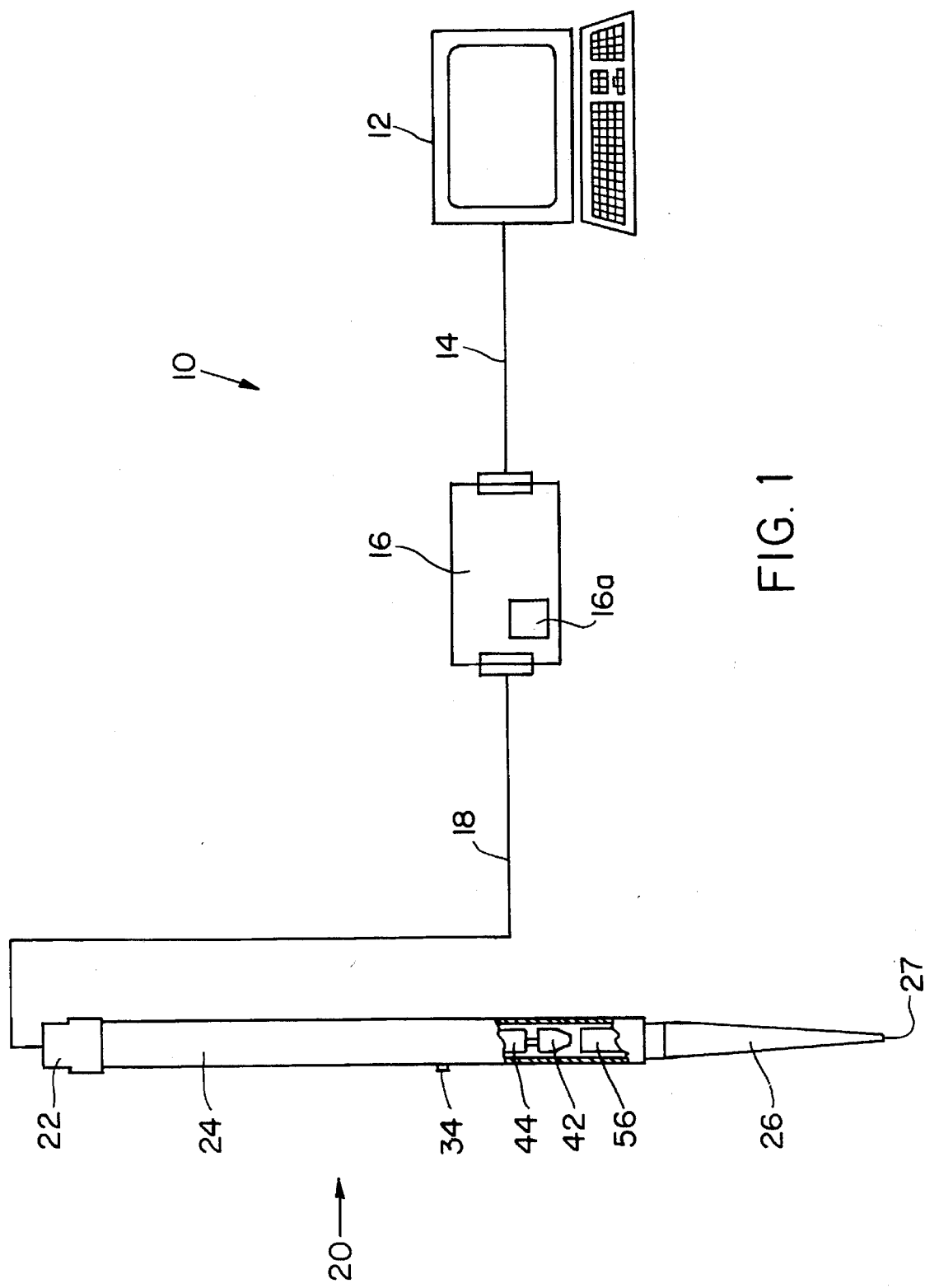
FIG. 1 is a schematic drawing of the present invention dental analyzer with a portion of the dental probe broken away.

Referring to FIG. 1, dental analyzer 10 includes a dental probe 20, an electronics box 16 and a computer or processor 12. Dental probe 20 impacts crown 76 of dental implant 28 (FIG. 2) and measures the acceleration time history of the dental implant as the dental implant vibrates from the impact. Dental probe 20 has a probe body 24 for housing an actuator 44, a hammer 42 extending from actuator 44 and an accelerometer 56. The accelerometer 56 is secured to a rigid, light weight probe tip 26 which in use is positioned against the crown 76 of dental implant 28. Probe tip 26 and accelerometer 56 are supported by a flexible diaphragm or membrane 58 (FIG. 11) stretched over the distal end of probe body 24. The diaphragm 58 serves to press probe tip 26 against crown 76 of dental implant 28 and isolates motion of the probe tip 26 and accelerometer 56 from motion of probe body 24. Actuator 44 includes an electromagnetic coil 45 and a spring 40. A firing button 34 activates actuator 44 which brings hammer 42 into spring 40 which returns the hammer against the accelerometer 56. This causes probe tip 26 to transfer the impact energy into the dental implant 28 causing the dental implant to vibrate. Accelerometer 56 can then measure the acceleration time history of the vibrating dental implant 28.

Dental probe 20 is electrically connected to electronics box 16 by electrical connector 22 and line 18. The electronics box 16 includes a capacitive storage power source 16a for providing power to actuator 44. As presented in greater detail below with regard to FIG. 5, electronics box 16 also includes signal conditioning filters for conditioning or filtering the acceleration time histories measured with dental probe 20 to remove unwanted signals. Electronics box 16 and dental probe 20 also contain amplifiers for amplifying the accelerating time history signal. Electronics box 16 is connected to computer 12 by line 14. Computer 12 converts the conditioned acceleration time histories provided to it by electronics box 16 into a frequency spectrum through a Fourier transform function. A diagnosis of the condition of the dental implant 28 can then be made from the frequency spectrum.

Opto-isolation buffers within electronics box 16 isolate the 110 volt electronics of computer 12 from dental probe 20 for patient safety. The computer can be of the portable type which uses harmless low voltage (less than 5 v) causing no danger to the patient. Furthermore, the electronics box can operate with similar harmless voltage precluding the use of opto-isolators.

Figure 2:
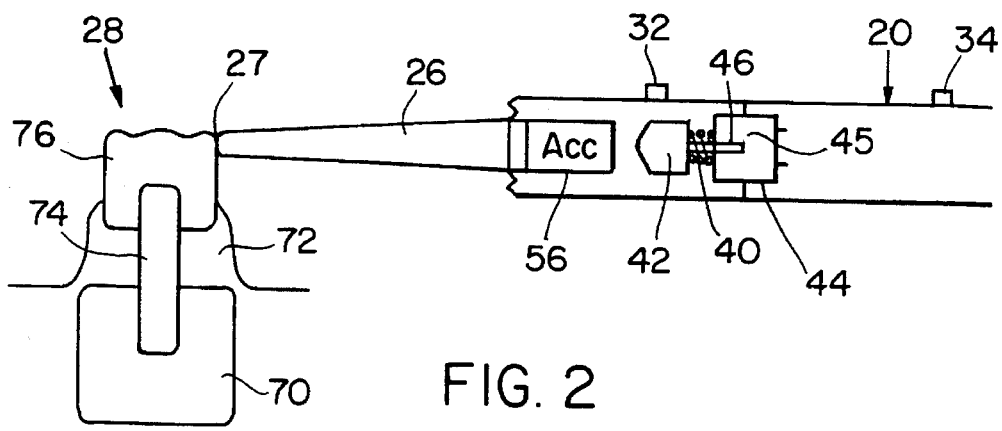
FIG. 2 is a schematic drawing of the dental probe positioned against a dental implant.
Figure 11:
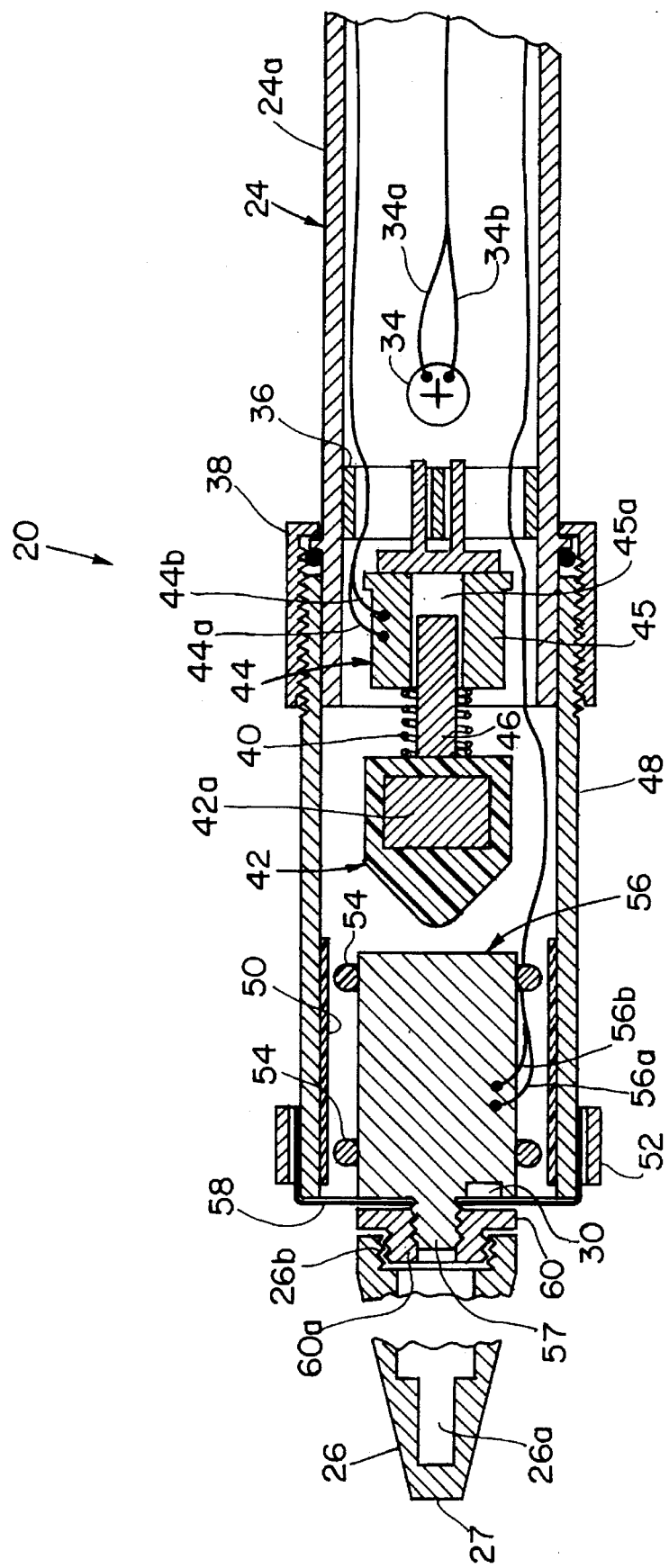
FIG. 11 is a side sectional view of a portion of the dental probe.

In operation, referring to FIG. 2, dental probe 20 is held in the hand of a dentist or dental technician and the end 27 of probe tip 26 is pressed against crown 76 of dental implant 28 stretching diaphragm 58 (FIG. 11). Dental implant 28 consists of a crown 76 secured to the jaw bone 70 by implant post 74. The end 27 of probe tip 26 is positioned against the crown 76 of dental implant 28 above gum tissue 72. Glue or wax can be used to prevent the end 27 of probe tip 26 from moving or losing contact with crown The firing button 34 is then depressed in order to provide power to actuator 44 which activates the hammer 42. However, power will not be provided to actuator 44 until force sensor 30 (FIG. 11) detects that probe tip 26 is pressed against dental implant 28 with a predetermined/presetable force. Alternatively, force sensor 30 can be substituted with a position sensor which allows power to be delivered to actuator 44 when diaphragm 58 has deflected enough so that accelerometer 56 is in a predetermined position relative to probe body 24. Once this predetermined force is attained, a pulse of power from the capacitive storage power source 16a in electronics box 16 is released to momentarily energize electromagnetic coil 45 of actuator 44. This draws hammer 42 into firing position toward the electromagnetic coil 45 and away from accelerometer 56, compressing spring 40.

Figure 3:
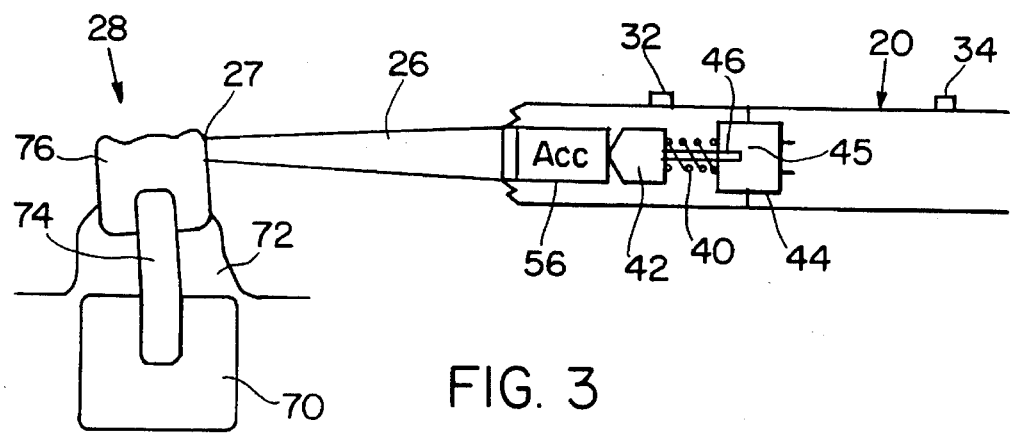
FIG. 3 is a schematic drawing of the dental probe impacting the dental implant.

After the energy in the capacitor has dissipated in the actuator, the electromagnetic coil 45 releases the potential energy of the compressed spring 40. Hammer 42 then strikes accelerometer 45 to provide a calibrated flat frequency response impact (FIG. 3). Since accelerometer 56 is rigidly secured to probe tip 26, probe tip 26 impacts against crown 76 to deflect implant post 74. By only firing hammer 42 when probe tip 26 is pressed against crown 76 of dental implant 28 with a predetermined force, dental probe 20 consistently delivers a constant impact. Indicator light 32 illuminates to provide an indication that an impact has occurred.

Figure 4:
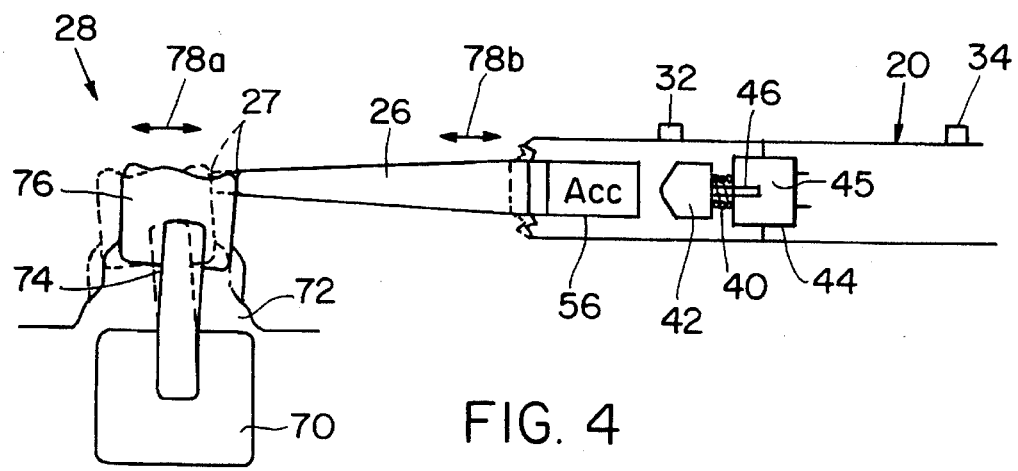
FIG. 4 is a schematic drawing of the dental probe positioned against a vibrating dental implant.

Once dental implant 28 has been impacted by probe tip 26, dental implant 28 oscillates back and forth as indicated by arrows 78a (FIG. 4). Hammer 42 provides a Dirac-Delta input function to dental implant 28 causing dental implant 28 to vibrate at a range of frequencies. Probe tip 26 remains pressed against crown 76 such that the end 27 of probe tip 26 remains in contact with crown 76. Diaphragm 58 allows probe tip 26 and accelerometer 56 to oscillate independently of probe body 24 while probe tip 26 remains pressed against crown 76. As a result, the probe tip 26 and accelerometer 56 vibrate in unison with dental implant 28 as shown by arrows 78b. This vibration is the complex dynamic resonance of the structure under test (the dental implant in this case) which when transformed to the frequency domain provides a spectral signature which is unique to the structure under test. It is also an extremely sensitive measurement because a measurement of frequency is the most accurate and resolute measurement that can be made in the field of electronics.

The accelerometer 56 measures accelerations of motion of the dental implant 28 to provide an acceleration time history of the dental implant 28 recorded in volts over time. The acceleration of dental implant 28 is measured by accelerometer 56 at 100 microsecond intervals which results in a total of about 1000 samples of data taken for an acceleration time history.

Figure 5:
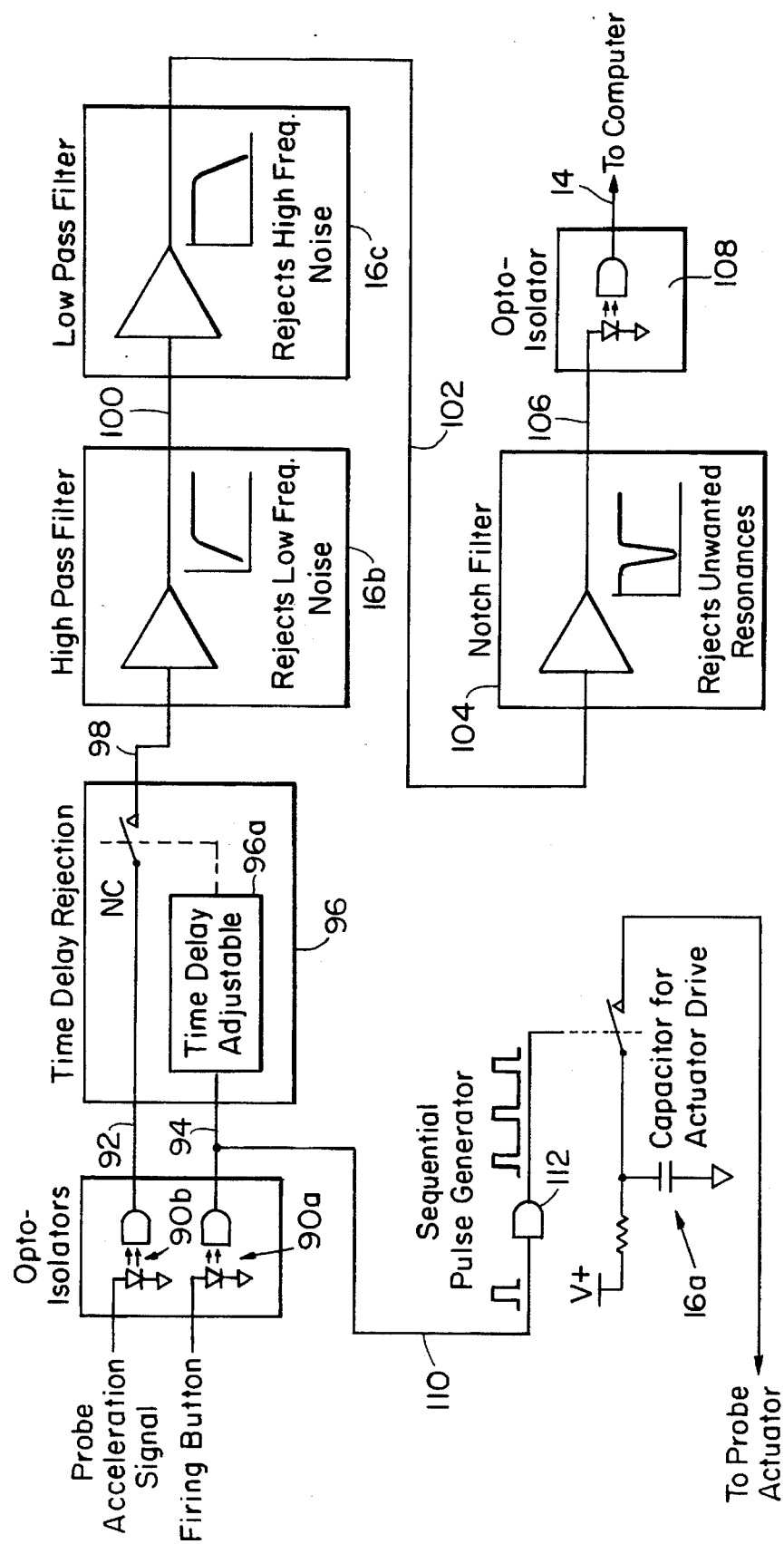
FIG. 5 is a schematic drawing of a preferred electrical circuit for the electronics box.

The electronics box 16 (FIG. 1) conditions the measured acceleration time history by rejecting non-useable data from the acceleration time history. FIG. 5 depicts a preferred electrical circuit for electronics box 16. A time delay 96 is connected to accelerometer 56 via opto-isolator 90b and line 92. Firing button 34 is connected to the adjustable time delay 96a of time delay 96 by opto-isolator 90a and line 94. Opto-isolators 90a and 90b electrically isolate dental probe 20 from electronics within electronics box 16. Firing button 34 is also connected to capacitor storage power source 16a via opto-isolator 90a, lines 94 and 110 and sequential pulse generator 112. High pass filter 16b is connected to time delay 96 by line 98. Low pass filter 16c is connected to high pass filter 16b by line 100. Notch filter 104 is connected to low pass filter 16c by line 102. Notch filter 104 is connected to computer 12 via line 106, opto-isolator 108 and line 104.

Figure 6:
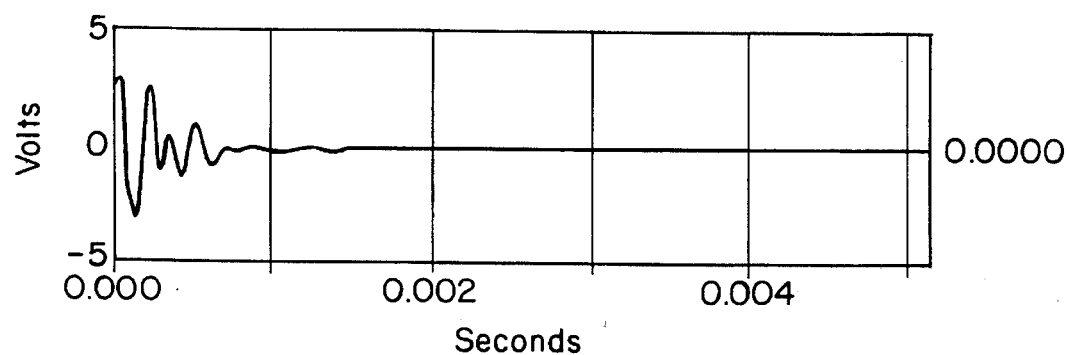
FIG. 6 is a graph of an acceleration time history for a dental implant.

When firing button 34 is depressed, sequential pulse generator 112 produces a series of pulses which discharges capacitive storage power source 16a into actuator 44. The pulses are spaced to allow a full time history measurement after each, and the multiple measurements may be averaged for improved signal to noise ratio. Once the crown 76 of dental implant 28 has been impacted, time delay 96 opens momentarily to reject the data generated by the initial impact of the probe tip 26 which is typically the first ½ cycle after impact against dental implant 28 so that only the data associated with the resulting vibration of dental implant 28 is recorded. Once the time delay 96 closes, the acceleration time history signal passes through high pass filter 16b where low frequency signals or noise (approximately 0 to 10 Hz) is filtered out. These low frequency signals are unusable, contain noise, and when rejected, increase the signal to noise ratio of the desired signal. The signal then passes through low pass filter 16c which rejects high frequency noise above the Nyquist sampling rate of the data acquisition system (5 kHz), thereby increasing again the signal to noise ratio of the desired signal. Notch filter 104 then rejects unwanted resonances. An optional sinx/x filter can be located after notch filter 104 to increase resolution through curve fitting extrapolation. The signal to noise ratio is further increased through data averaging of 3 or more successive samples of data taken within a 5 second period. The data from these successive samples is statistically averaged or route-summ-squared to provide a resultant signal with increase signal to noise ratio. FIG. 6 is a graph depicting the conditional acceleration time history of dental implant 28.

Figure 7:
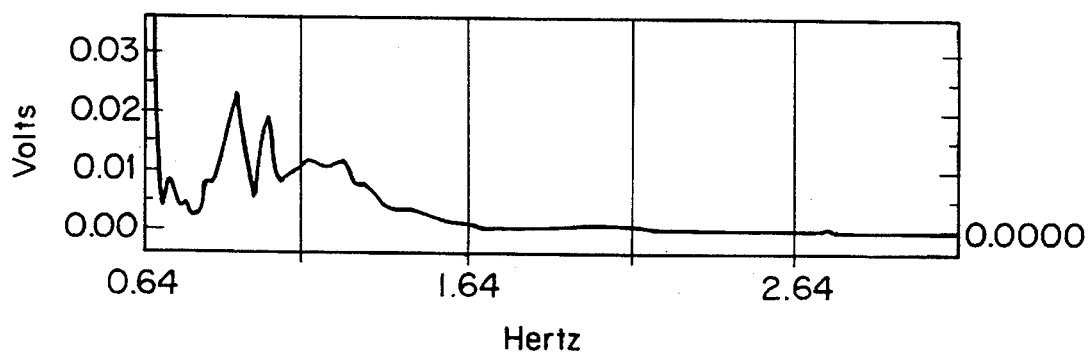
FIG. 7 is a frequency spectrum generated from the acceleration time history graph of FIG. 6.

The conditioned acceleration time history is then transferred from electronics box 16 to the computer 12 for processing. Computer 12 employs a standard commercially available software program to perform a frequency domain fast Fourier transform on the conditioned acceleration time history of dental implant 28 which converts the acceleration time history into a frequency spectrum recorded in volts versus frequency (FIG. 7). For each dental implant 28 which is measured, the corresponding frequency spectrum has a unique spectral signature similar to a fingerprint. As a result, each dental implant can be identified by its corresponding frequency spectrum. Additionally, information regarding the condition of the dental implant 28 can be mathematically extracted from the acceleration time history and the generated frequency spectrum.

Figure 8:
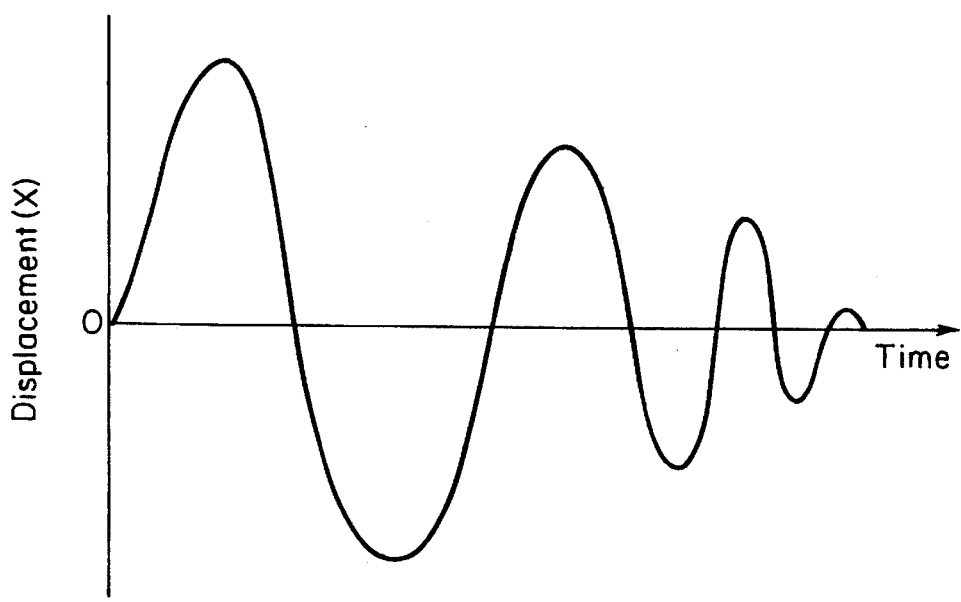
FIG. 8 is a one-dimensional position/displacement time history graph of a vibrating dental implant.

For example, the double integration of the conditioned acceleration time history of dental implant 28 provides the mobility or position of the dental implant 28 over time. This mobility or position of dental implant 28 can be plotted on a graph over time. Such a plot records the movement of dental implant 28 along a single dimension over time as seen in FIG. 8.

Figure 9:
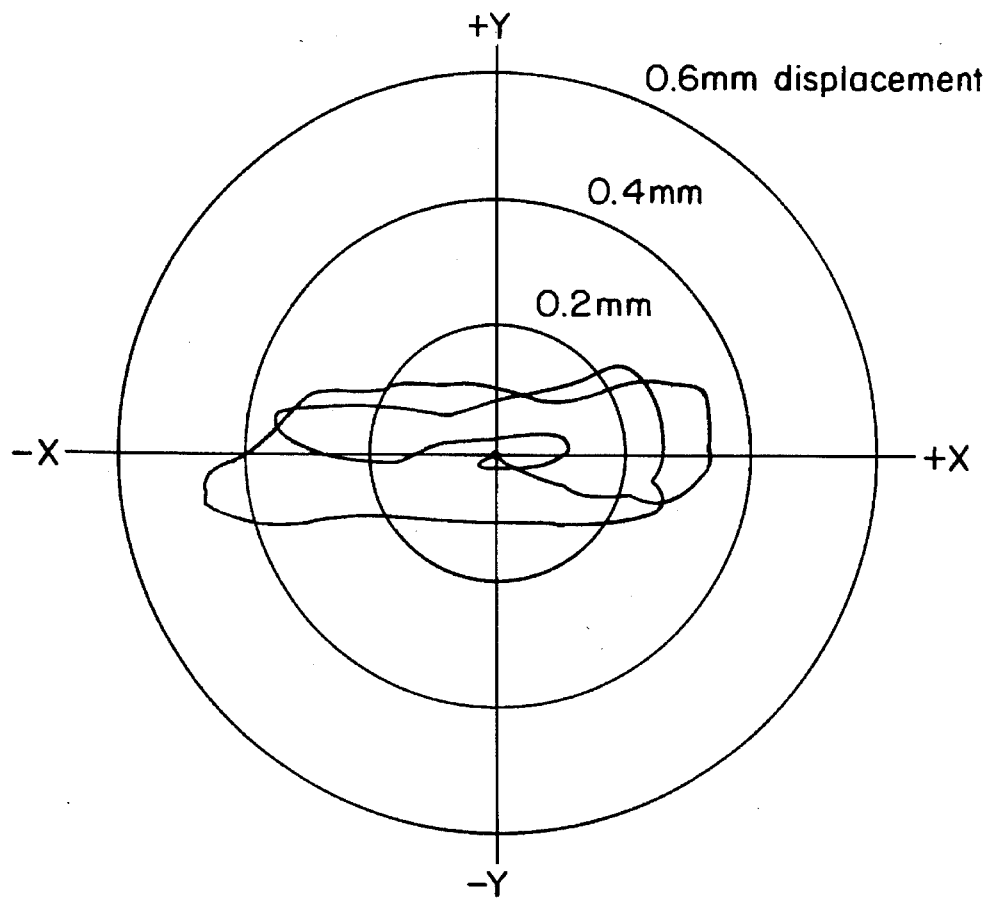
FIG. 9 is a two-dimensional position/displacement time history graph of a vibrating dental implant.
Figure 10:
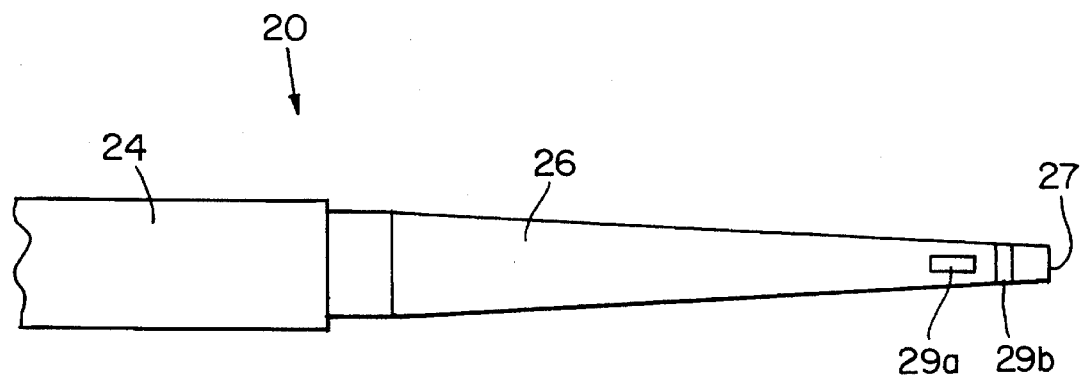
FIG. 10 is a side view of a preferred probe tip showing two accelerometers mounted to the probe tip.

An example of two dimensional mobility over time is seen in the position/displacement time history graph of FIG. 9 where the displacement of dental implant 28 is plotted in the x and y directions. The two-dimensional feature of the graph is preferably provided by securing a second accelerometer to the probe tip 26 orientated in a direction orthogonal to accelerometer 56. As a result, two acceleration time histories of dental implant 28 are measured in directions perpendicular to each other forming x and y components. A preferred configuration for measuring acceleration time histories in two directions is depicted in FIG. 10 where two accelerometers 29a and 29b are mounted in orientations perpendicular to each other near the end 27 of probe tip 26. A third accelerometer can be added for measuring acceleration time histories in a third direction in order to acquire three dimensional data. Alternatively, multiple accelerometers can be bonded directly to dental implant 28.

The velocity of the dental implant 28 can be determined by performing a single integration of the acceleration time history. This also can be plotted on a graph as a function of time.

The frequency spectrum also provides information regarding the condition of dental implant 28. For example, the damping of the dental implant 28 is mathematically determined by the rate at which the amplitude of a particular frequency of the frequency spectrum dies out over time.

After impact, the implant 28, probe tip 26 and accelerometer 56 vibrate together as a damped single degree of freedom oscillator that satisfies the following differential equation:

$$m\ddot{x} + c\dot{x} + kx = 0 \qquad \text{Equation 1}$$

where:
  m=mass
  c=damping coefficient
  k=spring rate
  x=tooth displacement

The homogenous solution of Equation 1 may be expressed for damping as:

$$x = e^{-\xi wt}\{A \sin wt + B \cos wt\} \qquad \text{Equation 2}$$

where:
  w=natural frequency of the oscillator (rad/sec)
  t=time (secs)
  A,B=coefficients that depend on the boundary conditions
  $\xi$=percent critical damping (c/Cc)

Applying the known boundary conditions at t=0 where x=0 and tooth velocity $V_o$=0 yields:
  B=0
  A=Vo/w Hence, the tooth vibration after impact is given by the expression:

$$x = V_o/w \ e^{-\xi wt} \sin wt \qquad \text{Equation 3}$$

$$x = f(t)$$

Equation 3 expresses the response displacement x as a function of time t. Note that x approaches zero as t approaches infinity due to the presence of the damping term:

$$e^{-\xi wt}$$

The presence of damping results in a decaying sinusoid.

The resonant frequencies of the dental implant 28 are indicated by the peaks in the frequency spectrum. Once the resonant frequencies are known, the mode shapes of dental implant 28 can be determined. By treating the dental implant 28 as a cantilever beam, the various known mode shapes of a vibrating cantilever beam can be correlated to each resonant frequency of dental implant 28.

The stiffness of dental implant 28 is determined by the equation:

$$k = w^2 m \qquad \text{Equation 4}$$

The Fourier transform function which transforms the acceleration time history from the time domain to the frequency domain is given by:

$$F(w) = \int_{\infty}^{\infty} e^{-iwt} f(t) dt \qquad \text{Equation 5}$$

Other information such as osseointegration and/or bond characteristics of the dental implant 28 and spectral discrimination are determined through spectral analysis in which the frequency spectrum of dental implant 28 is compared with a database of previously recorded frequency spectrums. The data base includes software identifying certain characteristics regarding dental implants with corresponding specific characteristics of the frequency spectrum.

Once the computer 12 matches features of the generated frequency spectrum with features found in frequency spectrums stored in the database, a diagnosis can be made regarding the condition of the dental implant 28. Information regarding the patient's age, sex and medical history can be entered into the computer 12 to aid in the diagnosis. In applications where a simple answer is desired, the diagnosis can be signalled by a red or green indicator light. In such a case, a green light would indicate that certain characteristics of the frequency spectrum are within an acceptable range and would designate that the implant is good. A red light would indicate that certain characteristics of the frequency spectrum are outside of an acceptable range and would designate that the implant is bad. In applications where more information is desired, the results of the diagnosis can be provided on the screen of computer 12 or printed out on a printer.

When following the osseointegration and/or bond characteristics of a particular dental implant 28 over time, the measured frequencies of the dental implant will shift to higher frequencies over a period of time if the bond between the dental implant and the bone improves over time. Conversely, a shift to lower frequencies will occur over time if the bond deteriorates.

FIG. 11 provides a more detailed depiction of dental probe 20. Probe body 24 consists of a main tube 24a and an extension tube 48. Extension tube 48 is secured to main tube 24a by a nut 38. The two piece probe body 24 allows longitudinal adjustment between the accelerometer 56 and the actuator 44.

Actuator 44 is secured to the distal end of main tube 24a by a "G" clip 36 which is preferably made of corrosion resistant spring steel. The "G" clip exerts an expansion force on the inner diameter of main tube 24a and allows the location of actuator 44 to be adjusted along the longitudinal axis of main tube 24a to calibrate dental probe 20. Alternatively, actuator 44 can be secured to main tube 24a by other suitable means such as by threading the interior of main tube 24a and securing actuator 44 with a threaded adapter.

Firing button 34 is electrically connected to electrical connector 22 by lines 34a and 34b. Actuator 44 is electrically connected to electrical connector 22 by lines 44a and 44b.

The head of hammer 42 is preferably made from a molded highly damped epoxy with an inner densaloy weight 42a for an ideal impact force. Hammer 42 has a ferromagnetic stem 46 which slides within bore 45a of electromagnetic coil 45. This ensures linear motion of hammer 42 along the longitudinal axis of probe body 24 when fired. Spring 40 is positioned about stem 46 and is positioned against both hammer 42 and electromagnetic coil 45.

The accelerometer 56 is small with a low mass such that accelerometer 56 does not substantially distort or alter the vibration of dental implant 28. Accelerometer 56 is electrically connected to electrical connector 22 by lines 56a and 56b. Two "O"-rings 54 are mounted around accelerometer 56 to keep the motion of accelerometer 56 along the longitudinal axis of probe body 24. A low friction sleeve 50 preferably made of polytetrafluoroethylene (PTFE) is positioned on the interior surface of extension tube 48 surrounding accelerometer 56. This ensures smooth undisturbed motion of accelerometer 56 such that the acceleration of accelerometer 56 is not significantly altered if the "O"-rings 54 contact low friction sleeve 50.

Diaphragm or membrane 58 is stretched over the distal end of extension tube 48 and is secured by a force ring 52. Diaphragm 58 is preferably made from surgical rubber 0.007 inches thick but alternately can be of other suitable thicknesses and elastic materials. Threaded neck 57 extends through diaphragm 58 and is threaded into adapter 60 which sandwiches diaphragm 58 between the adapter 60 and the accelerometer 56, thereby securing accelerometer 56 to diaphragm 58. Diaphragm 58 isolates motion of the probe tip 26, adapter 60 and accelerometer 56 from the motions of the probe body 24 so that only the motions of dental implant 28 are measured by accelerometer 56.

Probe tip 26 has a female threaded portion 26b which mounts onto the male threaded portion 60a of adapter 60. Probe tip 26 is hollow having a cavity 26a to reduce the mass of probe tip 26. The end 27 of probe tip 26 has a non-slip flat surface for positioning against dental implant 28. The diameter of end 27 is typically small which can be, for example, 0.1 inches in diameter. A long tip of about 2.5 inches is preferable for measuring deep within a patient's mouth while a shorter pointed tip is preferable for testing bone structure through layers of skin. Probe tip 26 is typically disposable for health considerations. Adapter 60 and probe tip 26 have wrench flats which allow probe tip to be tightened on to adapter 60 with a wrench. It is preferable that probe tip 26 have a transfer function of unity or 1 over the bandwidth analyzed so that the collected data is not distorted.

In the preferred embodiment, dental probe 20 is about 6 inches long and 0.5 inches wide which makes it suitable for hand held use. The probe body 24, probe tip 26, adapter 60 and nut 38 are preferably made of titanium for reduced weight. However, alternatively, other suitable materials such as stainless steel, aluminum or plastic can be used.

In other applications, the present invention can be used for analyzing other medical implants such as hip implants, knee implants, elbow implants, shoulder implants, wrist implants or any other medical orthopedic implant. Structures covered by skin, cartilage or hair can be analyzed by employing a pointed probe tip which penetrates the covering material and becomes in intimate contact with the structure below. Additionally, the present invention can be used to analyze organic structures of a patient such as teeth or bones, for example, vertebrae, ribs or limb bones.

Figure 12:
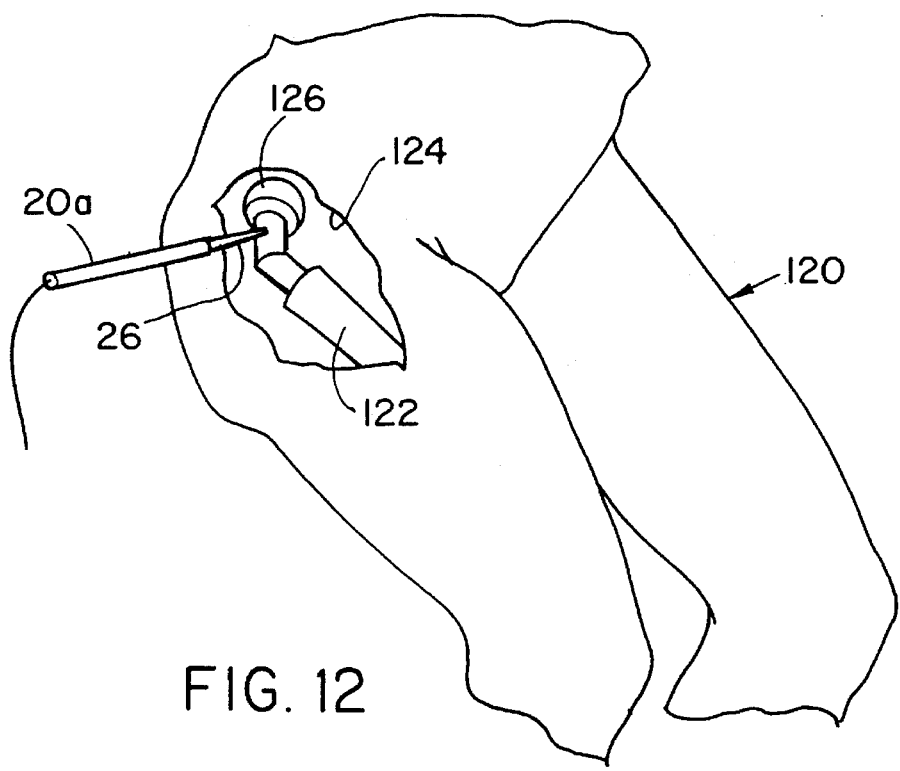
FIG. 12 is a schematic drawing of the present invention probe positioned against a hip implant.

When analyzing a medical implant, the medical implant can be analyzed during installation before the surgical wound is closed. FIG. 12 depicts an example of a hip implant 126 being analyzed prior to closure of the surgical wound. The femur bone 122 and the newly installed hip implant 126 are exposed by the open surgical wound 124 in patient 120. A probe 20a which is similar probe 20, has a probe tip 26 positioned against hip implant 126. The acceleration time history of the hip implant 126 is measured by probe 20a and converted into a frequency spectrum in the same manner as described above with respect to dental implant 28. The frequency spectrum of hip implant 126 is compared to a clinical data base containing previously stored frequency spectrums for hip implants. Characteristics of the frequency spectrum for hip implant 126 are compared with characteristics of the stored frequency spectrums. The clinical data base includes acceptable ranges for certain characteristics of frequency spectrums which correlate to acceptable clinical standards for a hip implant. If the frequency spectrum of hip implant 126 correlates to lower than acceptable clinical standards, hip implant 126 is likely to be poorly attached due to inadequate cementation, cartilage or soft tissue inclusion in the receptor site, or a crack in the receptor site, etc. This condition alerts the surgeon of the need for correcting the problem before the wound 124 is closed which eliminates the need for a second procedure when the hip implant fails.

Figure 13:
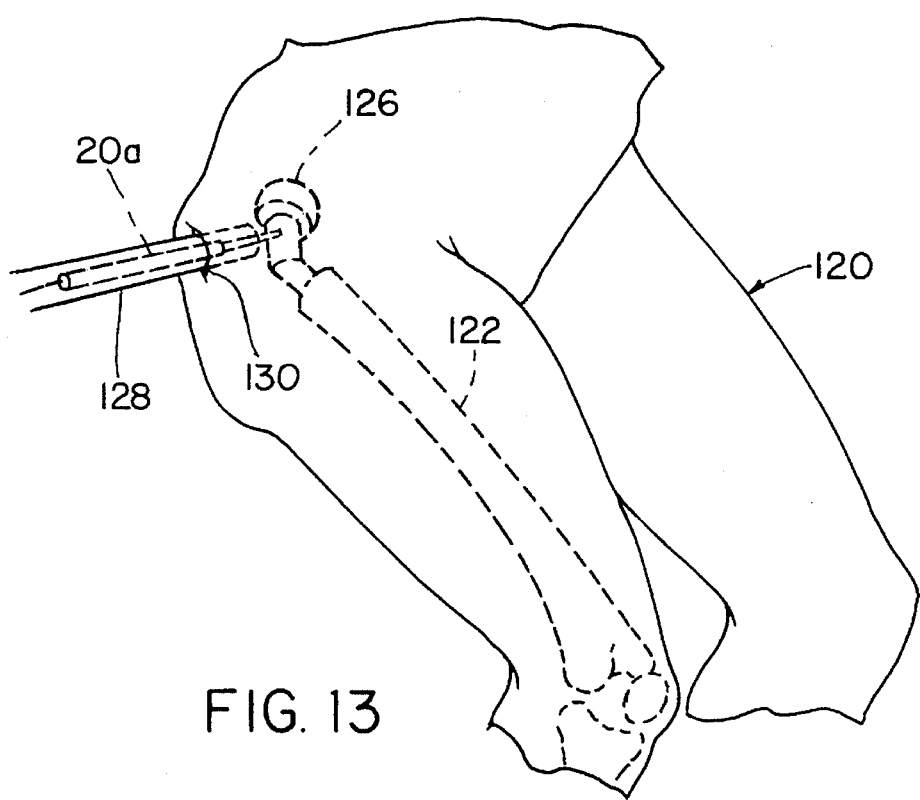
FIG. 13 is a schematic drawing of the present invention probe positioned against a hip implant with the aid of an endoscope.

Referring to FIG. 13, hip implant 126 can be analyzed after the wound 124 is closed through arthroscopic techniques. In such a procedure, probe 20a is incorporated into the tip of an endoscope 128. The endoscope 128 is inserted into the patient 120 through an incision 130 and probe 20a is positioned against hip implant 126, thereby allowing probe 20a to analyze hip implant 126. This allows measurements of hip implant 126 to be conducted over a long period of time. The frequency spectrums of hip implant 126 taken over a period of time can be compared against each other to determine whether hip implant 126 is becoming more stable or deteriorating. By detecting small changes before they become major problems, interceptive therapy may be instituted in an attempt to avoid prosthesis replacement.

The present invention apparatus can also be used in the industry for determining the structural characteristics of mechanical structures such as airplane wings, machinery, or structural buildings using vibration signature analysis for predictive maintenance. In such a case, the probe would be employed to impact and measure the acceleration time history of the structure at a desired location on the structure. The frequency spectrum would then be generated from the acceleration time history. In many engineering applications, only the frequency spectrum is needed. However, alternatively, previously measured acceleration time histories and their corresponding frequency spectrums can be stored in a database for comparison with measured acceleration time histories and corresponding frequency spectrums.

Figure 14:
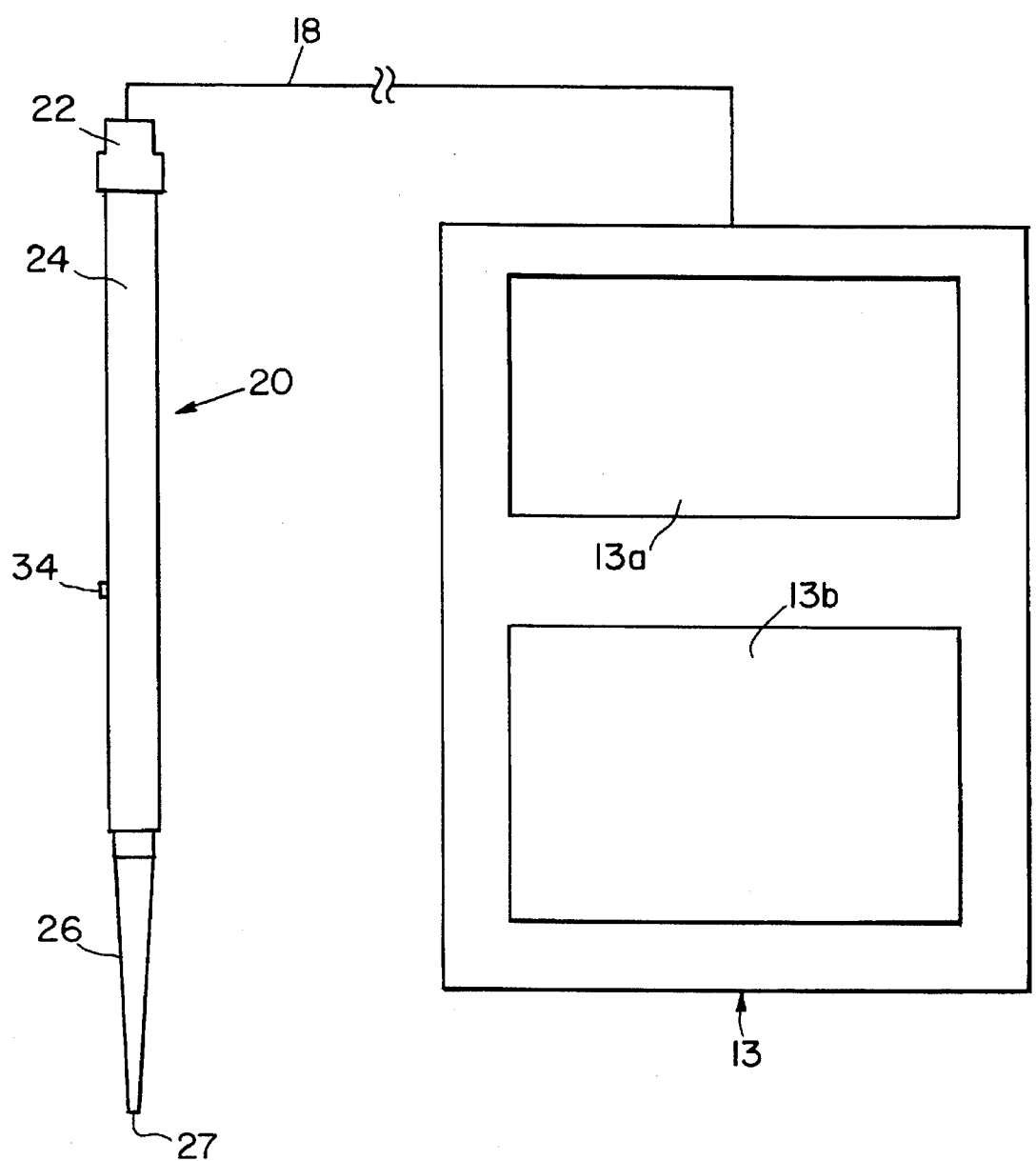
FIG. 14 is a schematic drawing of another preferred embodiment of the present invention.

FIG. 14 depicts a system suitable for industrial maintenance or other applications where a portable unit is desirable. The system includes a probe 20 which is coupled to a portable computer 13. Portable computer 13 is small enough to be hand-held or worn on a belt and includes a screen 13a for viewing acceleration time histories and frequency spectrums. A keypad 13b allows the user to input information. The electronics for conditioning the acceleration time history are included within portable computer 13.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims. For example, although actuator 44 is described to be electromechanically operated, alternatively, actuator 44 can be pneumatically or mechanically operated. Additionally, the accelerometer can be substituted with a velocity or a position sensor for measuring the velocity or position of probe tip 26. Furthermore, the electronics of electrical box 16 can be incorporated into computer 12. Also, the open wound and arthroscopic analyzing techniques depicted in FIGS. 12 and 13 can be used to analyze any type of medical implant as well as to analyze a patient's bones.

What is claimed is:

1. A probe comprising:

a probe tip for contacting a structure;

an accelerometer coupled to the probe tip for measuring an acceleration time history of the structure;

a hammer for impacting the probe tip against the structure, the probe tip being mechanically isolated from the hammer such that the probe tip can move independently from the hammer after the structure is impacted; and an actuator for firing the hammer.

2. The probe of claim 1 further comprising:

a probe body comprising a hollow tube for housing the actuator; and a membrane secured to the probe body and supporting the accelerometer for isolating motion of the accelerometer from motion of the probe body.

3. The probe of claim 1 in which the actuator comprises:

an electromagnetic coil for positioning the hammer into firing position; and a spring positioned against the hammer for firing the hammer.

4. The probe of claim 1 further comprising a sensor for preventing the actuator from firing the hammer until the probe tip contacts the structure at a predetermined force.

5. The probe of claim 1 further comprising a processor for converting the measured acceleration time history of the structure into a frequency spectrum.

6. The probe of claim 1 in which the structure is a dental implant.

7. A probe comprising:

a probe tip for contacting a structure;

an accelerometer coupled to the probe tip for measuring an acceleration time history of the structure;

a hammer for impacting the probe tip against the structure;

an actuator for firing the hammer;

a probe body comprising a hollow tube for housing the actuator; and a membrane secured to the probe body supporting the accelerometer for isolating motion of the accelerometer from motion of the probe body.

8. The probe of claim 7 in which the actuator comprises:

an electromagnetic coil for positioning the hammer into firing position; and a spring positioned against the hammer for firing the hammer.

9. The probe of claim 7 further comprising a sensor for preventing the actuator from firing the hammer until the probe tip contacts the structure at a predetermined force.

10. The probe of claim 7 further comprising a processor for converting the measured acceleration time history of the structure into a frequency spectrum.

11. The probe of claim 7 in which the structure is a dental implant.

12. A method of measuring dynamic characteristics of a structure comprising the steps of:
    positioning a probe tip against the structure, the probe tip being secured to an accelerometer;
    impacting the probe tip against the structure with a hammer to initiate dynamic resonance of the structure, the probe tip remaining in contact with the structure during dynamic resonance of the structure; and
    measuring an acceleration time history of the structure with the accelerometer.

13. The method of claim 12 further comprising the step of firing the hammer with an actuator.

14. The method of claim 13 further comprising the step of preventing the actuator from firing the hammer until the probe tip contacts the structure at a predetermined force.

15. The method of claim 13 further comprising the steps of:
    housing the actuator within a hollow probe body; and
    supporting the accelerometer on a membrane secured to the probe body for isolating motion of the accelerometer from motion of the probe body.

16. The method of claim 12 in which firing the hammer with the actuator comprises the steps of:
    positioning the hammer into firing position with an electromagnetic coil; and
    firing the hammer with a spring positioned against the hammer.

17. The method of claim 12 further comprising the step of converting the measured acceleration time history of the structure into a frequency spectrum.

18. The method of claim 12 in which the structure is a dental implant.

19. The method of claim 17 further comprising the step of comparing characteristics of the frequency spectrum with a database of frequency spectrums.

20. The method of claim 12 further comprising the step of adhering the probe tip to the structure.

21. The method of claim 12 further comprising the step of mechanically isolating the probe tip from the hammer such that the probe tip can move independently from the hammer after the structure is impacted.

22. A method of measuring dynamic characteristics of a structure comprising the steps of:
    positioning a probe tip against the structure, the probe tip being secured to an accelerometer;
    firing a hammer with an actuator, the actuator being housed within a hollow probe body;
    impacting the probe tip against the structure with the hammer; and
    measuring an acceleration time history of the structure with the accelerometer, the accelerometer being supported on a membrane secured to the probe body for isolating motion of the accelerometer from motion of the probe body.

23. The method of claim 22 further comprising the step of preventing the actuator from firing the hammer until the probe tip contacts the structure at a predetermined force.

24. The method of claim 22 in which firing the hammer with the actuator comprises the steps of:
    positioning the hammer into firing position with an electromagnetic coil; and
    firing the hammer with a spring positioned against the hammer.

25. The method of claim 22 further comprising the step of converting the measured acceleration time history of the structure into a frequency spectrum.

26. The method of claim 22 in which the structure is a dental implant.

27. The method of claim 25 further comprising the step of comparing the frequency spectrum with a database of frequency spectrums.

28. A method of measuring dynamic characteristics of a structure comprising the steps of:
    positioning a probe tip against the structure, the probe tip being secured to an accelerometer;
    impacting the probe tip against the structure to initiate dynamic resonance of the structure, the probe tip remaining in contact with the structure during dynamic resonance of the structure;
    measuring an acceleration time history of the structure with the accelerometer; and
    converting the measured acceleration time history of the structure into a frequency spectrum.

29. A method of determining dynamic characteristics of a medical implant comprising the steps of:
    impacting the medical implant with a probe tip to initiate dynamic resonance of the structure, the probe tip remaining in contact with the structure during dynamic resonance of the structure;
    measuring the acceleration time history of the medical implant with an accelerometer coupled to the probe tip; and
    converting the measured acceleration time history into a frequency spectrum.

30. The method of claim 29 further comprising the step of comparing characteristics of the frequency spectrum with a data base of frequency spectrums.

31. A probe comprising:
    a probe tip for contacting a structure;
    a sensor coupled to the probe tip for measuring motion characteristics of the structure;
    a hammer for impacting the probe tip against the structure;
    an actuator for firing the hammer;
    a probe body comprising a hollow tube for housing the actuator; and
    a membrane secured to the probe body supporting the sensor for isolating motion of the sensor from motion of the probe body.

32. A system for measuring dynamic characteristics of a structure comprising:
    a hand-held probe having a probe body and a probe tip, the probe tip for impacting the structure, the probe tip being substantially mechanically isolated from the probe body such that the probe tip can move independently from the probe body, an accelerometer coupled to the probe tip measuring the acceleration time history of the structure; and
    a processor for converting the measured acceleration time history of the structure into a frequency spectrum.

33. The system of claim 32 in which the frequency spectrum has a spectral signature.

34. A method of measuring dynamic characteristics of a structure comprising the steps of:
    positioning a probe tip against the structure, the probe tip being secured to an accelerometer;
    impacting the probe tip against the structure with a hammer;

mechanically isolating the probe tip from the hammer such that the probe tip can move independently from the hammer after the structure is impacting; and measuring an acceleration time history of the structure with the accelerometer.

35. A probe comprising:

a probe tip for contacting a structure;

a sensor coupled to the probe tip for measuring motion characteristics of the structure;

a hammer for impacting the probe tip against the structure, the probe tip being mechanically isolated from the hammer such that the probe tip can move independently from the hammer after the structure is impacted;

an actuator for firing the hammer; and a probe body comprising a hollow tube for housing the actuator.

* * * * *